United States Patent
Colussi et al.

(10) Patent No.: US 8,361,750 B2
(45) Date of Patent: Jan. 29, 2013

(54) **RBSA FROM *K. LACTIS* EXPRESSION, SECRETION AND PURIFICATION OF RECOMBINANT BOVINE SERUM ALBUMIN (RBSA) FROM *K. LACTIS* AND USES THEREOF**

(75) Inventors: Paul A. Colussi, Gloucester, MA (US); Thomas C. Evans, Jr., Topsfield, MA (US); Christopher H. Taron, Essex, MA (US)

(73) Assignee: New England Biolabs, Inc., Ipswich, MA (US)

( * ) Notice: Subject to any disclaimer, the term of this patent is extended or adjusted under 35 U.S.C. 154(b) by 654 days.

(21) Appl. No.: 12/294,759

(22) PCT Filed: Mar. 30, 2007

(86) PCT No.: PCT/US2007/007921
§ 371 (c)(1), (2), (4) Date: Sep. 26, 2008

(87) PCT Pub. No.: WO2007/123689
PCT Pub. Date: Nov. 1, 2007

(65) Prior Publication Data
US 2010/0240099 A1    Sep. 23, 2010

Related U.S. Application Data

(60) Provisional application No. 60/788,850, filed on Apr. 3, 2006, provisional application No. 60/875,917, filed on Dec. 20, 2006.

(51) Int. Cl.
*C12P 21/00* (2006.01)
*C07K 14/765* (2006.01)
*C12N 9/16* (2006.01)

(52) U.S. Cl. .................. 435/69.6; 435/196; 530/363

(58) Field of Classification Search .................. None
See application file for complete search history.

(56) References Cited

U.S. PATENT DOCUMENTS
2006/0088868 A1    4/2006    Evans et al.

FOREIGN PATENT DOCUMENTS
WO    03/059846    7/2003
WO    2006/066595    6/2006
WO    2006066595 A2  *  6/2006

OTHER PUBLICATIONS

Saliola et al (Use of the KIADH4 Promoter for Ethanol-Dependent Production of Recombinant Human Serum Albumin in *Kluyveromyces lactis* Appl Environ Microbiol. Jan. 1999; 65(1):53-60).*
Fleer et al Stable multicopy vectors for high-level secretion of recombinant human serum albumin by *Kluyveromyces* yeasts. Biotechnology (NY) Oct. 1991(9(10):968-975.*
Lee et al. Appl Microbiol Biotechnol. 44:425-31 (1995).
Antoni et al. Ital. J. Biochem. 31:100-6 (1982).
Trujillo et al., Biotechniques 9:620-2 (1990).
Metcalf et al. Biochem. J. 199:465-72 (1981).
Amersham Pharmacia Biotech: Biodirectory 2000 catalog. p. 106 (2000).
Doyle, E. et al., Molecular Plant-Microbe Interactions, 15(6):549-556 (2002).
Hilger, C. et al., clinical and Experimental Immunology, 123(3) 387-394 (2001).
Camargo, et al., Animal Reproduction, 3(1):19-28 (2006).
Mckeown, B., Biotechniques, 17(2):246-248 (1994).
Fleer, R. et al., Bio/technology, 9(10):968-975 (1991).
Lee et al. Applied Microbiology Biotechnology 1995.
Antoni et al. Italian Journal of Biochemistry 31 2 100-106 , 1982.

* cited by examiner

*Primary Examiner* — Kagnew H Gebreyesus
(74) *Attorney, Agent, or Firm* — New England Biolabs, Inc.; Harriet M. Strimped

(57) ABSTRACT

A recombinant BSA (rBSA) that (a) substantially lacks deoxyribonuclease activity as determined by incubating rBSA with linear DNA overnight and gel electrophoresis, (b) lacks animal viruses associated with animal-derived cell growth supplements; and (c) is capable of stabilizing DNA proteins is provided. Methods for making the rBSA and using it to stabilize enzymes are also provided.

8 Claims, 3 Drawing Sheets

SEQUENCE LISTING

```
<160> NUMBER OF SEQ ID NOS: 2

<210> SEQ ID NO 1
<211> LENGTH: 39
<212> TYPE: DNA
<213> ORGANISM: unknown
<220> FEATURE:
<223> OTHER INFORMATION: primer

<400> SEQUENCE: 1
ccgctcgaga aaagaagggg tgtgtttcgt cgagataca                         39

<210> SEQ ID NO 2
<211> LENGTH: 40
<212> TYPE: DNA
<213> ORGANISM: unknown
<220> FEATURE:
<223> OTHER INFORMATION: primer

<400> SEQUENCE: 2
ataagaatgc ggccgcttag gctaaggctg tttgagttga                        40
```

RBSA FROM *K. LACTIS* EXPRESSION, SECRETION AND PURIFICATION OF RECOMBINANT BOVINE SERUM ALBUMIN (RBSA) FROM *K. LACTIS* AND USES THEREOF

CROSS REFERENCE

This application is a §371 application of international application number PCT/US2007/007921 filed Mar. 30, 2007, which claims priority from U.S. provisional applications No. 60/788,850 filed on Apr. 3, 2006 and 60/875,917 filed on Dec. 20, 2006, herein incorporated by reference.

BACKGROUND

Bovine serum albumin (BSA) is used as a diluent or a blocking agent in numerous applications including ELISAs (Enzyme-Linked Immunosorbent Assay), blots and immunohistochemistry. Additionally, native BSA is routinely used to enhance the stability of proteins during or after their purification, or in biological assays and to prevent adhesion of the enzyme to reaction tubes and other vessels.

In recent years, there has been a mounting concern over the use of animal products in many pharmaceutical and biotech industry applications because of the threat of animal viruses and transmissible sponge-form ensephelopathies (TSEs; the causative agent of mad cow disease) that may be present in bovine-derived BSA. Current methods of preparation of BSA involve purification of the protein from bovine plasma and testing for the presence of these contaminating agents. However, testing can only detect known viruses or TSEs and does not uncover infectious agents that have not yet been discovered. Therefore, there is currently no alternative large-scale supply of BSA that is assured to be free of all animal-derived infectious agents. Additionally, until this work, it was unclear whether a recombinant BSA (rBSA) would possess the same protein stabilizing characteristics as its native counterpart.

SUMMARY

In one embodiment, an rBSA preparation is provided that (a) substantially lacks deoxyribonuclease activity as determined by incubating rBSA with linear DNA overnight and by gel electrophoresis, (b) lacks animal viruses associated with animal-derived cell growth supplements; and (c) is capable of stabilizing DNA proteins. The rBSA may be expressed and secreted by a yeast production strain such as a *Kluyveromyces* here exemplified by *K. lactis*. In addition, the rBSA preparation may further include a phosphate buffer.

In an embodiment of the invention, the reaction mixture may include an rBSA as described above and a DNA protein such as a restriction endonuclease. The reaction mixture may also include 50% glycerol.

In an embodiment of the invention, a method is provided for stabilizing DNA proteins that includes adding to a preparation of the DNA protein an rBSA preparation that (a) substantially lacks deoxyribonuclease activity as determined by incubating rBSA with DNA overnight and by gel electrophoresis, (b) lacks animal viruses associated with animal-derived cell growth supplements; and (c) is capable of stabilizing DNA proteins.

In an embodiment of the invention, a method is provided for making an rBSA preparation for stabilizing DNA proteins that includes (a) recombinantly expressing the rBSA in a *Kluyveromyces* strain such as *K. lactis* in an animal-free medium; and (b) heat-treating the purified rBSA.

BRIEF DESCRIPTION OF THE DRAWINGS

In FIG. 2A(i) no albumin has been added and the enzyme is less stable than in the presence of heat-treated albumin such that that cleavage does not occur effectively using 0.25 units of PvuI enzyme. In 2A(ii) addition of heat-treated native BSA results in cleavage using 0.06 units of PvuI enzyme. In 2A(iii), non-heat-treated rBSA results in non-specific nuclease cleavage of DNA. In 2A(iv), heat-treated rBSA results in cleavage by 0.06 units of PvuI.

DETAILED DESCRIPTION OF THE EMBODIMENTS

In an embodiment of the invention, a preparation of rBSA is provided that is substantially free of deoxyribonuclease activity, as determined by gel electrophoresis of a DNA preparation following an overnight incubation in the presence of rBSA, and further lacks animal virus contaminants associated with animal derived cell growth supplements. The rBSA is provided in a buffer suitable for adding to DNA binding enzymes so as to stabilize such enzymes. An example of a buffer suitable for use in the preparation is a phosphate buffer having a pH 6-8. rBSA as described herein can be made in quantities suitable for industrial scale-up in yeast cells such as *Kluyveromyces* sp.

In an embodiment of the invention, *Kluyveromyces* is selected as a host cell for expressing rBSA and secreting it into the culture media. *Kluyveromyces* has an advantage over other host organisms including other fungi because it appears not to secrete deoxyribonucleases as determined by overnight incubation with DNA. In contrast, *Aspergillus*, which is a filamentous fungus used as a host cell (WO 2006/066595), appears to secrete at least one deoxyribonuclease (Lee et al. *Appl Microbiol Biotechnol*. 44:425-31 (1995)).

Figure 3:
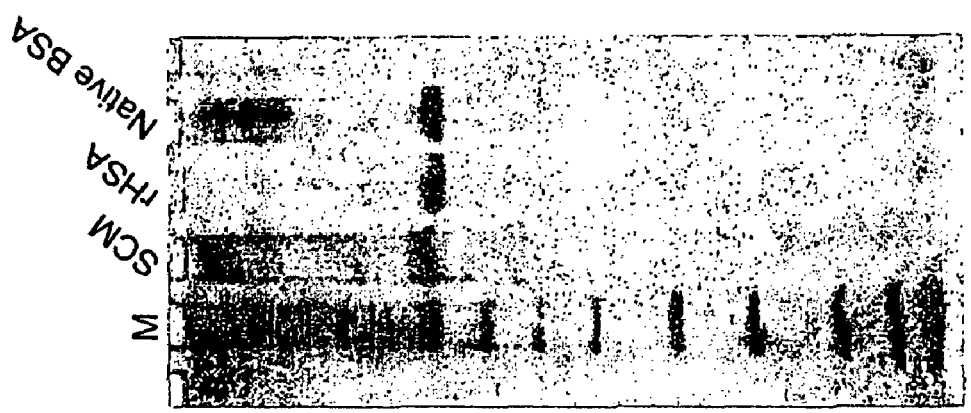
FIG. 3 shows a gel in which the purity of rHSA is assessed. 5 µl of spent fermentation broth containing rHSA, 2 µg of rHSA and 2 µg of native BSA (NEB B9001S, NEB, Ipswich, Mass.) were resolved on a 4-20% Tris-Glycine gel and stained with Coomassie Blue to show that the rHSA formed a single band containing an amount commensurate with the amount of total protein added.

Surprisingly, despite the apparent lack of secreted deoxyribonucleases in *Kluyveromyces* sp., rBSA from *K. lactis* was here found to co-purify with one or more deoxyribonucleases that caused non-specific degradation of DNA when the rBSA was added to a restriction endonuclease preparation used for specifically cleaving DNA (FIG. 3). While not wishing to be limited by theory, it is here suggested that the deoxyribonuclease activity is either an intrinsic property of the recombinant BSA protein or results from a cellular deoxyribonuclease that may have become physically associated with rBSA during its secretion from the host cell.

Removing deoxyribonuclease activity from native BSA using acetylation has been reported (Trugillo et al., *Biotechniques* 9:620-2 (1990)). Acetylated BSA can be problematic for in vitro stabilization of certain thermophilic DNA polymerase activities. In such reactions, the acetyl group can be transferred from BSA to the polymerase eliminating the enzyme's ability to catalyze DNA polymerization.

Example 2 provides a method of removing deoxyribonucleases from rBSA that involves heat treatment of purified rBSA. This eliminates deoxyribonuclease activity without the need for chemical modification of the protein by acetylation. rBSA produced via this method is capable of stabilizing a restriction endonuclease without causing degradation of the DNA substrate by the deoxyribonuclease (Example 3).

Native BSA from bovine blood serum like HSA from human serum has been long known to non-specifically bind and transport a myriad of molecules such as steroid hormones, fatty acids, small hydrophobic molecules, and ions in blood. Unlike HSA, the primary use for BSA has been for molecular biology applications where BSA is utilized for purposes that differ from its normal biological function. It is unknown how BSA performs these functions and how native BSA can stabilize the activity of enzymes it does not normally encounter in nature. For example, BSA purified from bovine serum can stabilize and enhance the in vitro activity of dozens of bacterial restriction endonucleases. In view of the uncertainty regarding the structure-function relationship of native BSA, it is unpredictable whether (a) purified rBSA made in non-bovine host cells might retain the same enzyme stabilizing ability as the protein purified from bovine blood serum; (b) certain molecules present in bovine serum are required additively or synergistically for native BSA to perform these functions; and (c) a rBSA produced by yeast and grown in animal free medium could be used in molecular biology applications such as stabilizing DNA proteins. "DNA proteins" are here intended to include those proteins or enzymes that act upon DNA. Examples of DNA proteins include restriction endonucleases, nicking endonucleases, methylases, DNA polymerases, RNA polymerases, helicases and DNA repair enzymes such as described in U.S. published application US-2006-0088868-A1.

Figure 2:
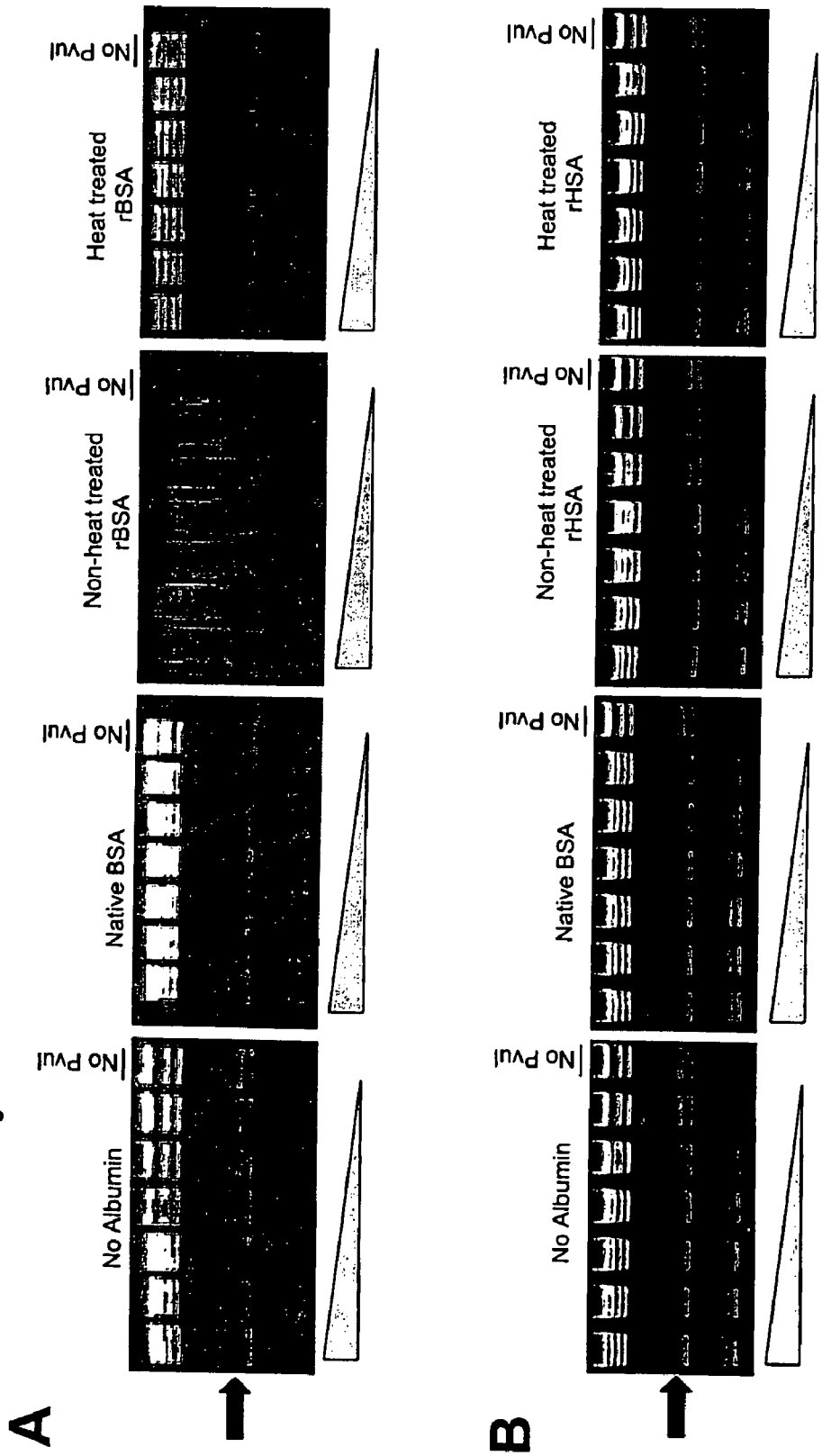
FIGS. 2A(i-iv) and 2B(i-iv) show a series of 8 gels where each gel has seven lanes. The lanes represent serial dilutions of PvuI. From the left of the gel, the amount of PvuI added to DNA is 5 units, 1 unit, 0.5 units, 0.25 units, 0.125 units, 0.06 units, no PvuI and a DNA marker.
FIGS. 2B(i) and (ii) are the same as 2A(i) and 2A(ii). 2B(iii) is non-heat-treated recombinant human serum albumin (rHSA) added to PvuI where nuclease activity does not appear to occur but the PvuI shows a similar lack of stability observed for 2A(i) and 2B(i). Heat-treated rHSA protects the stability of PvuI.

Another interesting feature of BSA is the high degree of amino acid sequence identity between HSA and BSA (76%). Nonetheless, the functional properties of these two proteins appear to significantly differ. For example, native HSA and native BSA behave differently with respect to their ability to bind an immobilized dye (Antoni et al. *Ital. J. Biochem.* 31:100-6 (1982)). Additionally, in the presence of a long-chain fatty acid HSA dissociation from an immobilized dye increases 3 fold whereas BSA dissociation increases about 15 fold (Metcalf et al. *Biochem. J.* 199:465-72 (1981)). These differences are consistent with the findings in Example 4 that *K. lactis*-expressed rBSA co-purifies with a deoxyribonuclease activity that is absent *K. lactis*-expressed rHSA. Moreover, while DNA is stable in the presence of non-heat-treated rHSA, DNA was destroyed in the presence of non-heat-treated rBSA (FIGS. 2A(iii) and B(iii)).

Considered together, these observations illustrate that despite the high degree of amino acid sequence identity, there are inherent measurable biochemical and physical differences between rHSA and rBSA. Thus, it was not possible to predict how well or even if recombinantly expressed HSA or BSA could function like native HSA or BSA as non-specific enzyme stabilizers. In fact, we have shown in FIG. 2, that purified heat-treated rBSA and rHSA are able to stabilize the activity of the restriction endonuclease PvuI without degradation of the DNA substrate (Example 4, FIG. 2).

rBSA expressed by *Kluyveromyces* species in animal-free medium provides an improved composition and method for stabilizing DNA proteins.

All references cited above and below, including priority applications U.S. provisionals Ser. No. 60/788,850 filed Apr. 3, 2006 and Ser. No. 60/875,917 filed Dec. 20, 2006, are incorporated by reference.

EXAMPLES

Example 1

Expression and Secretion of rBSA in *K. lactis*

The gene encoding BSA was amplified from bovine liver polyA+ RNA (Clontech, Mountain View, Calif.) using RT-PCR with the following forward and reverse primers, respectively: 5'-CCGCTCGAGAAAAGAAGGGGTGTGTTTCGTCGAGATACA (SEQ ID NO:1) and 5'-ATAAGAATGCGGCCGCTTAGGCTAAGGCTGTTTGAGTTGA (SEQ ID NO:2). The forward and reverse primers contain the engineered restriction enzyme sites XhoI and NotI, respectively (underlined). Additionally, the forward primer incorporates DNA sequence encoding the dibasic *K. lactis* Kex1 protease cleavage site KR (bold). The reverse primer also incorporates a stop codon (bold italics) and BSA encoding DNA in both primers is represented in italics. The BSA signal sequence was identified using SignalP software. Improved prediction of signal peptides (Bendtsen et al. *J. Mol. Biol.*, 340:783-795 (2004) and Nielsen et al. *Protein Engineering* 10:1-6 (1997) predicts that signal peptidase cleavage occurs between amino acids 18 and 19 (Ser18-Arg19). Thus, the DNA sequence encoding BSA in the forward primer began at the Arg19 codon. BSA DNA amplification was performed with the high-fidelity DNA Polymerase Deep Vent (New England Biolabs, Inc., Ipswich, Mass.) under the following cycling conditions: 94° C. for 5 min, 80° C. for 1 min, 94° C. for 30 sec, 58° C. for 30 sec, 72° C. for 2 min for 30 cycles, and finally 72° C. for 10 min. The gene encoding BSA was cloned into the XhoI and NotI restriction sites of the *K. lactis* expression vector pKLAC1 (New England Biolabs, Inc., Ipswich, Mass.), linearized with SacII and transformed into chemically competent *K. lactis* GG799 cells (New England Biolabs, Inc., Ipswich, Mass.). Transformants were selected on agar plates containing 5 mM acetamide at 30° C. for 4 days. A number of colonies were re-streaked on agar plates containing 5 mM acetamide for analysis of genomic integration of the expression cassette. Whole cell PCR was carried out on re-streaked transformants using primers specific for the identification of strains containing multiple integrated copies of the expression cassette. Transformant cells were pretreated in 25 μl of a 10 mg/ml lyticase solution in 1 M sorbitol for 1 h at 37° C. Fifteen microliters of lyticase-treated cells were used as template for a PCR reaction containing Integration primer 2 (New England Biolabs, Inc., Ipswich, Mass., Cat. No. S1278S) and Integration primer 3 (New England Biolabs, Inc., Ipswich, Mass. Cat No. S1279S) in a total reaction volume of 100 μl. The PCR reaction mixture was incubated at 95° C. for 10 minutes, then for 2 minutes at 80° C. at which time Taq DNA Polymerase (New England Biolabs, Inc., Ipswich, Mass.) was added. The PCR then proceeded with the following cycling conditions: 95° C. for 30 sec, 50° C. for 30 sec, 72° C. for 3 min for 30 cycles, and finally 72° C. for 10 min. Transformants identified as containing multiple integrated copies of the BSA expression cassette were further assessed for their ability to secrete rBSA. *K. lactis* strains were grown in 2 ml YPGal cultures for 4 days on a shaking platform incubator at 30° C. Spent culture medium was mixed with 3× Protein Loading Buffer (New England Biolabs, Inc., Ipswich, Mass.) and proteins were resolved by SDS-PAGE on 4-20% Tris-Glycine polyacrylamide gradient gels. BSA was identified as a 67 kDa protein following Coomassie staining.

Production of rBSA was carried out by fermentation of the strain producing rBSA in a 5 L working volume bench-top fermenter. A stock culture stored at −80° C. was thawed and used to inoculate 100 ml of defined fermentation medium (see composition below). A pre-culture was grown at 30° C. to a cell density ($OD_{600}$) of approximately 8 and used to start the fermentation. The defined batch fermentation medium was free of animal derived components and consisted of: $KH_2PO_4$ 8.873 g/L; $K_2HPO_4$ 1.724 g/L, Glucose 20 g/L, $MgSO_4.7H_2O$ 0.5 g/L, $(NH_4)SO_4$ 10 g/L, $CaCl_2.2H_2O$ 0.33 g/L, NaCl 1 g/L, KCl 1 g/L, $CuSO_4.5H_2O$ 0.005 g/L, $MnSO_4.H_2O$ 0.03 g/L, $Na_2MoO_4.2H_2O$ 0.008 g/L, $ZnCl_2$ 0.01 g/L, KI 0.001 g/L, $CoCl_2.6H_2O$ 0.002 g/L, $H_3BO_3$ 0.0004 g/L, $FeCl_3.6H_2O$ 0.015 g/L, Biotin 0.0008 g/L, Ca-pantothenate 0.02 g/L, Thiamine 0.015 g/L, Myo-inositol 0.016 g/L, Nicotinic Acid 0.010 g/L, and Pyridoxine 0.004 g/L. Sixty mL of the pre-culture broth was used to inoculate 3 L of batch medium. pH and temperature during the fermentations were maintained at 6° C. and 30° C., respectively. Air was sparged into the fermenter at a constant rate (5 rpm) and the dissolved oxygen (DO) was maintained at 30% of saturation by varying the agitation rate. The glucose in the batch medium was completely consumed in approximately 17 hours, at which time the glucose feeding stage was initiated. The feed medium was free of animal-derived components and consisted of: Glucose 448 g/L, $MgSO_4.7H_2O$ 6 g/L, $CaCl_2.2H_2O$ 1.65 g/L, NaCl 1 g/L, KCl 1 g/L, $CuSO_4.5H_2O$ 0.0075 g/L, $MnSO_4.H_2O$ 0.045 g/L, $Na_2MoO_4.2H_2O$ 0.012 g/L, $ZnCl_2$ 0.015 g/L, KI 0.0015 g/L, $CoCl_2.6H_2O$ 0.003 g/L, $H_3BO_3$ 0.0006 g/L, $FeCl_3.6H_2O$ 0.0225 g/L, Biotin 0.0032 g/L, Ca-pantothenate 0.080 g/L, Thiamine 0.060 g/L, Myo-inositol 0.064 g/L, Nicotinic Acid 0.040 g/L, and Pyridoxine 0.016 g/L. The glucose feed was introduced at an exponentially increasing rate to control the growth rate at approximately 0.12 $h^{-1}$. Approximately 1.1 L of glucose feed was added. This was followed by the galactose feeding stage. The galactose feed medium was the same as the glucose feed medium, except galactose was present at 448 g/L instead of glucose. Galactose sourced from plants (sugar beets) was used in place of galactose derived from bovine milk. Approximately 1.1 L of galactose feed was added at a constant rate of 40 mL/h. Total fermentation time was 65 hours.

Examples of other production strains of *Kluyveromyces* include *K. marxianus* variety *fragilis*. Other yeast production strains include *Tarrowia*, *Pichia*, *Hansenula* and *Saccharomyces*.

Example 2

Figure 1:
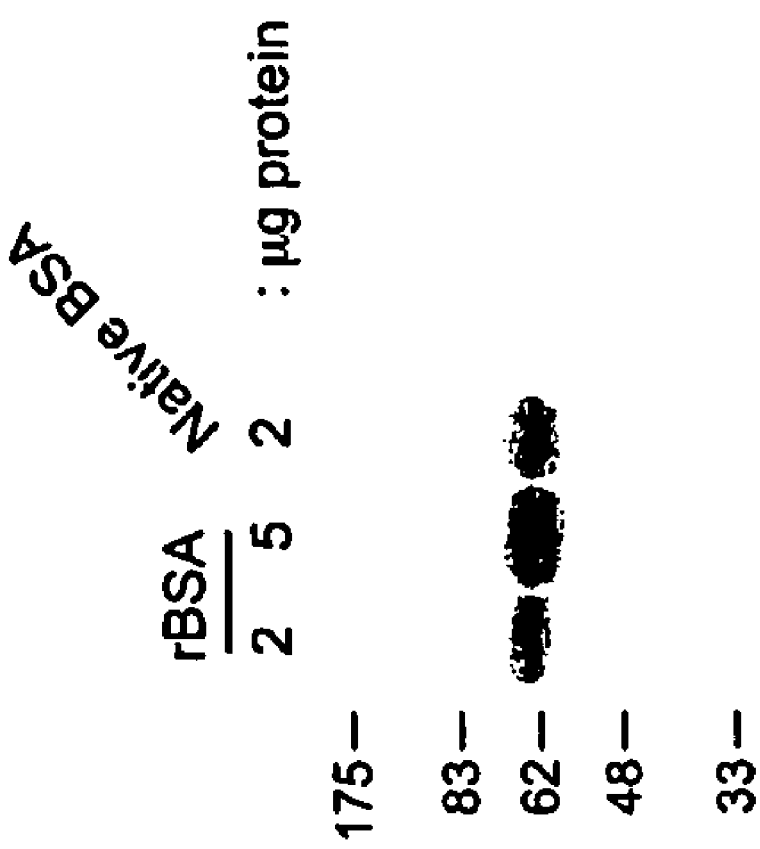
FIG. 1 shows a gel in which the purity of recombinant BSA is compared with the purity of the wild type protein. 2 µg and 5 µg of rBSA and 2 µg of native BSA ((NEB B9001S, New England Biolabs, Inc. (NEB), Ipswich, Mass.)) were resolved on a 4-20% Tris-Glycine gel and stained with Coomassie Blue to show that the rBSA formed a single band containing an amount commensurate with the amount of total protein added.

Purification of rBSA rBSA was purified from *K. lactis* spent culture medium by ion-exchange and size exclusion chromatography. Specifically rBSA was first bound to a DEAE column and eluted in a 50 mM-1M NaCl gradient in buffer A (50 mM Tris-Cl pH 7.5, 0.1 mM EDTA, 10 mM DTT and 5% glycerol). Fractions containing rBSA were identified following resolution of eluted proteins by SDS-PAGE and visualization of rBSA by Coomassie staining. Fractions containing rBSA were pooled and passed over a source Q column. Bound proteins were eluted in a 50 mM-1M NaCl gradient in buffer A. Fractions containing rBSA were identified following resolution of eluted proteins by SDS-PAGE and visualization of rBSA by Coomassie staining. Fractions containing rBSA were pooled and passed over a Superdex 75 size-exclusion column. Fractions containing rBSA were identified following resolution of fraction samples by SDS-PAGE and visualization by Coomassie staining. rBSA was concentrated to a working solution of 1 mg/ml. FIG. 1 shows that when resolved by SDS-PAGE purified rBSA migrates identically to bovine-derived BSA. To inactivate nuclease activity that co-purified with rBSA, purified rBSA (1 mg/ml) was heat-treated for 2 hours at 80° C. rBSA was subsequently filtered through a 0.22 μM filter.

Example 3

Stabilization of Restriction Endonuclease Function Using rBSA

To determine if rBSA could behave as an enzyme-stabilizing agent in the same manner as native bovine-derived BSA, a stability assay was performed using the restriction endonuclease PvuI. In this assay, 1 unit of PvuI was subjected to 2-fold serial dilutions in restriction digests containing 1 μg of HindIII-digested lambda DNA as a substrate in 50 mM Tris-HCl containing 100 mM NaCl, 10 mM $MgCl_2$, and 1 mM dithiothreitol. The reactions comprising each dilution series were supplemented with a final concentration of 0.1 μg $ml^{-1}$ purified native BSA (FIG. 2A(ii)), purified non-heat-treated rBSA (FIG. 2A(iii) or purified heat-treated rBSA). Reactions were incubated overnight at 37° C. and enzyme efficiency was determined following resolution of digested DNA on a 1% agarose gel and visualization by ethidium bromide staining. Incomplete digestion of the target DNA substrate was best observed by the appearance of a 2300 bp band (indicated by arrows in FIG. 2).

PvuI stability is compromised in the absence of BSA leading to a decrease in DNA cleavage efficiency (FIG. 2A(ii)). Addition of purified non-heat-treated rBSA resulted in nuclease degradation of the DNA substrate in all lanes (FIG. 2A(iii)). The presence of purified heat-treated rBSA stabilized PvuI activity to the same degree as purified native BSA.

An identical series of digests were also performed using purified non-heat treated rHSA (FIG. 2B third panel left) and purified heat-treated HSA (FIG. 2B right panel). Non-heat treated rHSA did not have a nuclease activity associated with it (FIG. 2B(iii)), but it also did not stabilize PvuI activity unless it was heat-treated (FIG. 2B(iv)).

These results demonstrate that purified heat-treated rBSA produced in *K. lactis* and purified from spent culture medium acts as an enzyme-stabilizing agent as efficiently as native bovine-derived BSA without the underlying risks associated with bovine-sourced BSA.

Example 4

Comparison of rBSA and rHSA rBSA was prepared and purified as described in Example 1.

Construction of a *K. lactis* strain that produces rHSA was previously described (Colussi & Taron *Appl. Environ. Microbiol.* 71:7092-8 (2005)). Fermentation of this strain was carried out in a 5 L working volume bench-top fermenter. A stock culture stored at −80° C. was thawed and used to inoculate 100 ml of defined fermentation medium. A pre-culture was grown at 30° C. to a cell density ($OD_{600}$) of approximately 8 and used to start the fermentation. The defined batch fermentation medium, which was also used for the pre-cultures, was the same as that used for the rBSA fermentation except 1 g/L of $MgSO_4.7H_2O$ was present. Forty mL of the pre-culture broth was used to inoculate 2 L of batch medium. pH and temperature during the fermentations were maintained at 6° C. and 30° C., respectively. Air was sparged into the fermenter at a constant rate (5 lpm) and the dissolved oxygen (DO) was maintained at 30% of saturation by varying the agitation rate. The glucose in the batch medium was completely consumed in approximately 17 hours, at which time the glucose feeding stage was initiated. The feed medium was the same as that used for the rBSA fermentation. The glucose feed was introduced at a linearly increasing rate and approximately 1.1 L of glucose feed was added. This was followed by the galactose feeding stage. The galactose feed medium was the same as that used for the rBSA fermentation. Approximately 1.1 L of galactose feed was added at a linearly increasing rate. Total fermentation time was 64 hours.

rHSA was purified from *K. lactis*-spent fermentation medium by ion-exchange and size exclusion chromatography. Specifically, rHSA was first passed through a 500 ml bed volume of DEAE HyperD resin that had been equilibrated in 20 mM Tris-Cl pH 8.0, 300 mM NaCl and 5% glycerol. The column was washed with an additional 500 ml of buffer to wash the void volume through the column. Approximately 2 liters of sample was subjected to volume reduction dialysis using 50 mm dialysis tubing overlayed with 500 grams of solid PEG 8000 for 12 hours at 4° C. The sample was then applied to a 44 ml bed volume of Biosep DEAE resin that has been equilibrated in 20 mM Tris-Cl pH 8.0, 50 mM NaCl and 5% glycerol. rHSA bound to the resin and was eluted using a linear gradient of NaCl ranging from 50 to 700 mM in 20 mM Tris-Cl pH 8.0 and 5% glycerol. The majority of rHSA eluted in a single fraction at 200 mM NaCl. This fraction was dialyzed against 20 mM Tris-Cl pH 8.0, 500 mM NaCl and 50% glycerol at 4° C. overnight and then subjected to gel filtration using a 1700 ml bed volume of Superdex75 pgXR 50/100 resin. The rHSA peak was the first to elute from this column. FIG. 3 shows that purified rHSA was homogeneous when separated by 4-20% SDS-PAGE and visualized by staining with Coomassie. rHSA was concentrated to a working solution of 1 mg/ml.

---

---

What is claimed is:

1. A preparation comprising:
    a purified heat-treated recombinant BSA obtained from a *Kluyveromyces* host cell fermentation that is free of animal viruses associated with animal derived cell growth supplements; and when compared with non-heat-treated recombinant BSA, lacks host cell non-specific deoxyribonuclease activity that degrades DNA.

2. The preparation according to claim 1, wherein the preparation comprises a phosphate buffer.

3. The preparation according to claim 1, capable of stabilizing a protein reagent, wherein the protein reagent is selected from the group consisting of a restriction endonuclease, a nicking endonuclease, a methylase, a DNA polymerase, an RNA polymerase, a helicase, and a DNA repair enzyme.

4. A reaction mixture preparation according to claim 3, further comprising 50% glycerol.

5. A method for making a rBSA preparation according to claim 1 for stabilizing DNA proteins, comprising:
    (a) recombinantly expressing the rBSA in *K. lactis* in an animal free medium; and
    (b) heat-treating the purified rBSA.

6. A method for stabilizing DNA proteins, comprising:
   (a) forming a preparation according to claim 1 and
   (b) obtaining the stabilized protein reagent.

7. A method for making an rBSA preparation according to claim 1, comprising:
   (a) recombinantly expressing the rBSA in *Kluyveromyces lactis* in an animal free medium; and
   (b) heat-treating the purified rBSA in the absence of a stabilizer.

8. A preparation according to claim 1, wherein the preparation lacks animal viruses.

* * * * *